(12) United States Patent
Gregory et al.

(10) Patent No.: US 12,734,291 B2
(45) Date of Patent: Sep. 15, 2026

(54) TIME DELAY MECHANISM FOR A HYDRAULIC DRUG DELIVERY DEVICE

(71) Applicant: MannKind Corporation, Danbury, CT (US)

(72) Inventors: Christopher Gregory, Hopkinton, MA (US); Geoffrey Jenkins, Dartmouth, MA (US)

(73) Assignee: MannKind Corporation, Danbury, CT (US)

( * ) Notice: Subject to any disclaimer, the term of this patent is extended or adjusted under 35 U.S.C. 154(b) by 0 days.

(21) Appl. No.: 18/342,118

(22) Filed: Jun. 27, 2023

(65) Prior Publication Data

US 2023/0338645 A1 Oct. 26, 2023

Related U.S. Application Data

(63) Continuation of application No. 17/670,262, filed on Feb. 11, 2022, now Pat. No. 11,730,883, which is a (Continued)

(51) Int. Cl.
*A61M 5/145* (2006.01)
*A61M 5/142* (2006.01)
*A61M 5/32* (2006.01)

(52) U.S. Cl.
CPC ........ *A61M 5/14248* (2013.01); *A61M 5/145* (2013.01); *A61M 5/14526* (2013.01); (Continued)

(58) Field of Classification Search
CPC .......... A61M 5/14526; A61M 5/14593; A61M 5/14248; A61M 2005/14252; (Continued)

(56) References Cited

U.S. PATENT DOCUMENTS 4,698,055 A 10/1987 Sealfon
5,971,953 A * 10/1999 Bachynsky ....... A61M 5/31596 604/181

(Continued)

FOREIGN PATENT DOCUMENTS

CA 2646324 A1 10/2007
CA 2799784 A1 12/2011

(Continued)

OTHER PUBLICATIONS

International Search Report for International Application No. PCT/US2018/038518 dated Aug. 30, 2018, 2 pages.

(Continued)

*Primary Examiner* — Chelsea E Stinson
(74) *Attorney, Agent, or Firm* — Morgan, Lewis & Bockius LLP

(57) ABSTRACT

A medicament delivery device may comprise a medicament chamber configured to hold a medicament, a plunger configured to move relative to the medicament chamber to expel the medicament from the medicament chamber, a pin configured to move from a first pin position wherein the pin prevents movement of the plunger to a second pin position wherein the pin allows movement of the plunger, an actuation assembly configured to move the pin from the first pin position to the second pin position, and a needle coupled to the medicament chamber. The medicament may flow through the needle from the medicament chamber to a user. The actuation assembly may be configured to automatically move the pin after a predetermined time delay.

9 Claims, 15 Drawing Sheets

Related U.S. Application Data continuation of application No. 16/615,150, filed as application No. PCT/US2018/038518 on Jun. 20, 2018, now Pat. No. 11,278,667.

(60) Provisional application No. 62/522,649, filed on Jun. 20, 2017.

(52) U.S. Cl.
CPC ............ *A61M 5/1454* (2013.01); *A61M 5/32* (2013.01); *A61M 2005/14252* (2013.01)

(58) Field of Classification Search
CPC ........... A61M 2005/14256; A61M 2005/1426; A61M 2005/14272
See application file for complete search history.

(56) References Cited

U.S. PATENT DOCUMENTS

| | | | | |
|---|---|---|---|---|
| 6,544,233 | B1 * | 4/2003 | Fukui | A61M 5/31596 604/220 |
| 7,455,663 | B2 | 11/2008 | Bikovsky | |
| 7,914,499 | B2 * | 3/2011 | Gonnelli | A61M 5/3298 604/151 |
| 2008/0103490 | A1 * | 5/2008 | Edwards | A61M 5/2033 604/890.1 |
| 2011/0060274 | A1 * | 3/2011 | Kuhn | A61M 5/284 604/82 |
| 2011/0098580 | A1 | 4/2011 | Mikhail et al. | |
| 2011/0306929 | A1 * | 12/2011 | Levesque | A61M 5/14248 604/150 |
| 2013/0317477 | A1 * | 11/2013 | Edwards | A61M 5/2466 604/82 |
| 2016/0082182 | A1 | 3/2016 | Gregory et al. | |
| 2017/0340827 | A1 | 11/2017 | Nazzaro et al. | |
| 2018/0043089 | A1 | 2/2018 | Nazzaro | |

FOREIGN PATENT DOCUMENTS

| | | | | |
|---|---|---|---|---|
| CA | 2845367 | A1 | 3/2013 | |
| CN | 203419202 | U | 2/2014 | |
| CN | 104582755 | A | 4/2015 | |
| DE | 102004055870 | A1 * | 5/2006 | A61M 5/31511 |

OTHER PUBLICATIONS

Written Opinion for International Application No. PCT/US2018/038518 dated Aug. 30, 2018, 6 pages.

Canadian Office Action dated Jan. 1, 2021 for Canadian Patent Application No. 3,065,558, 4 pages.

Decision of Rejection issued in corresponding Chinese Patent Application No. 201880038063.2, dated Aug. 22, 2022, with English translation.

* cited by examiner

TIME DELAY MECHANISM FOR A HYDRAULIC DRUG DELIVERY DEVICE

CROSS REFERENCE TO RELATED APPLICATIONS

This application is a continuation of U.S. application Ser. No. 17/670,262 filed Feb. 11, 2022, which is a continuation of U.S. application Ser. No. 16/615,150 filed Nov. 20, 2019, now U.S. Pat. No. 11,278,667, which is a U.S. National Stage Application that claims the benefit of International PCT Application No. PCT/US18/38518 filed Jun. 20, 2018, which claims the benefit of U.S. Provisional Patent Application No. 62/522,649 filed Jun. 20, 2017 entitled "Time Delay Mechanism for a Hydraulic Drug Delivery Device", each of which is incorporated by reference herein in its entirety.

BACKGROUND OF THE INVENTION

The present invention generally relates to a drug delivery device and, more particularly, to a time delay mechanism for a drug delivery device.

BRIEF SUMMARY OF THE INVENTION

In one embodiment there is a medicament delivery device that may comprise a medicament chamber configured to hold a medicament, a plunger configured to move relative to the medicament chamber to expel the medicament from the medicament chamber, a pin configured to move from a first pin position wherein the pin prevents movement of the plunger to a second pin position wherein the pin allows movement of the plunger, an actuation assembly configured to move the pin from the first pin position to the second pin position, and a needle coupled to the medicament chamber. The medicament may flow through the needle from the medicament chamber to a user. The actuation assembly may be configured to automatically move the pin after a predetermined time delay.

The actuation assembly may comprise an adapter coupled to the pin and an activator configured to move the adapter from a first adapter position to a second adapter position, thereby moving the pin from the first pin position to the second pin position. The adapter may include an internal opening configured to receive at least a portion of the pin. The adapter may include a deflectable flange configured to engage a rim of the pin.

In a further embodiment, the actuation assembly may comprise a gear having an internal opening configured to receive the adapter. The adapter may be configured to move relative to the gear. The internal opening of the gear may be defined by a threaded perimeter wall and the adapter may comprise an external thread configured to mate with the threaded perimeter wall. The activator may be configured to rotate the gear and the adapter may be configured to move relative to the gear as the gear rotates. The activator may comprise a motor.

In a further embodiment, the medicament delivery device may include a drive gear coupled to the motor, the drive gear configured to mesh with the gear such that the motor rotates the gear as the motor rotates the drive gear. The medicament delivery device may further include a housing configured to receive at least a portion of the medicament chamber, the plunger, and the pin. The actuation assembly may be detachably coupled to the housing. The adapter may be rotationally fixed relative to the housing.

The actuation assembly may further include an engagement member coupled to the adapter, the engagement member configured to move relative to the adapter from a first engagement member position to a second engagement member position; and a catch configured to prevent movement of the engagement member when the engagement member is in the first engagement position. The adapter may be moveable from the first adapter position to the second adapter position when the engagement member may be in the second engagement member position. The activator may include a biasing element configured to urge the engagement member toward the second engagement member position.

In a further embodiment, the delivery device may include an actuator configured to move the engagement member from the first engagement member position to the second engagement member position.

In one embodiment there is a medicament delivery device that may comprise a first chamber including a first plunger, the first plunger configured to move relative to the first chamber and a second chamber fluidly connected to the first chamber. The second chamber may be configured to receive fluid from the first chamber when the first plunger moves relative to the first chamber. The medicament delivery device may include a third chamber including a third plunger, the third chamber fluidly connected to the first chamber. The third chamber may be configured to contain a medicament and the third plunger may be configured to move relative to the third chamber when the first plunger moves relative to the first chamber. The medicament delivery device may include a biasing element configured to move the first plunger relative to the first chamber and a needle coupled to the third chamber. The needle may be configured to provide a pathway for the medicament to flow from the third chamber to a user as the third plunger moves relative to the third chamber.

The first chamber may be configured to receive a fluid, wherein at least a portion of the fluid may be transferred from the first chamber to the second chamber as the first plunger moves relative to the first chamber. The second chamber may include a second plunger configured to move relative to the second chamber as the fluid is transferred from the first chamber to the second chamber. The second chamber may include a flexible membrane configured to move relative to the second chamber as the fluid is transferred from the first chamber to the second chamber. The second chamber may include an expandable membrane configured to expand relative to the second chamber as the fluid is transferred from the first chamber to the second chamber. The second chamber may include a gas permeable membrane configured to allow gas to escape from the second chamber but prevent fluid from exiting the second chamber as the fluid is transferred from the first chamber to the second chamber. At least a portion of the fluid may be transferred from the first chamber to the third chamber as the first plunger moves relative to the first chamber. The medicament delivery device may be configured to transfer the fluid from the first chamber to the second chamber before the fluid is transferred from the first chamber to the third chamber.

The medicament delivery device may be configured such that there may be a time delay between a time when first piston begins to move relative to the first chamber and the third piston begins to move relative to the third chamber. The first chamber may include a bypass, wherein the fluid flows through the bypass before transferring from the first chamber to the third chamber. The first plunger may include a first collar having a first collar diameter and a body having a body diameter, wherein the body diameter is less than the first collar diameter. The first plunger may include a second collar having a second collar diameter, wherein the body diameter is less than the second collar diameter. The second collar diameter may be substantially the same as the first collar diameter. The first chamber may include a distal portion between a distal end of the first chamber and the first collar, and the first chamber may include a proximal portion between the first collar and the second collar. Fluid may flow from the distal portion through the bypass and into the proximal portion as the first plunger moves relative to the first chamber. Fluid may be transferred from the proximal portion of the first chamber into the third chamber.

The second chamber may be fluidly connected to the first chamber by a first passage having a first passage diameter, the third chamber may be fluidly connected to the first chamber by a second passage having a second passage diameter, and the first passage diameter may be smaller than the second passage diameter. The first passage may include a first passage length, the second passage may include a second passage length, and the first passage length may be greater than the second passage length. The first passage length may be greater than the second passage length by an amount equal to or greater than a third chamber diameter. A volumetric flow rate of the fluid from the first chamber to the second chamber may be smaller than a volumetric flow rate of the fluid from the first chamber to the third chamber. Transfer of fluid into the third chamber may move the third plunger relative to the third chamber thereby expelling the medicament from the third chamber through the needle and to the user.

The medicament delivery device may include a pin configured to move from a first pin position wherein the pin prevents movement of the first plunger to a second pin position wherein the pin allows movement of the first plunger relative to the first chamber. The actuation assembly may be configured to move the pin from the first pin position to the second pin position.

BRIEF DESCRIPTION OF THE SEVERAL VIEWS OF THE DRAWINGS

The following detailed description of the time delay mechanism for a drug delivery device will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Figure 1:
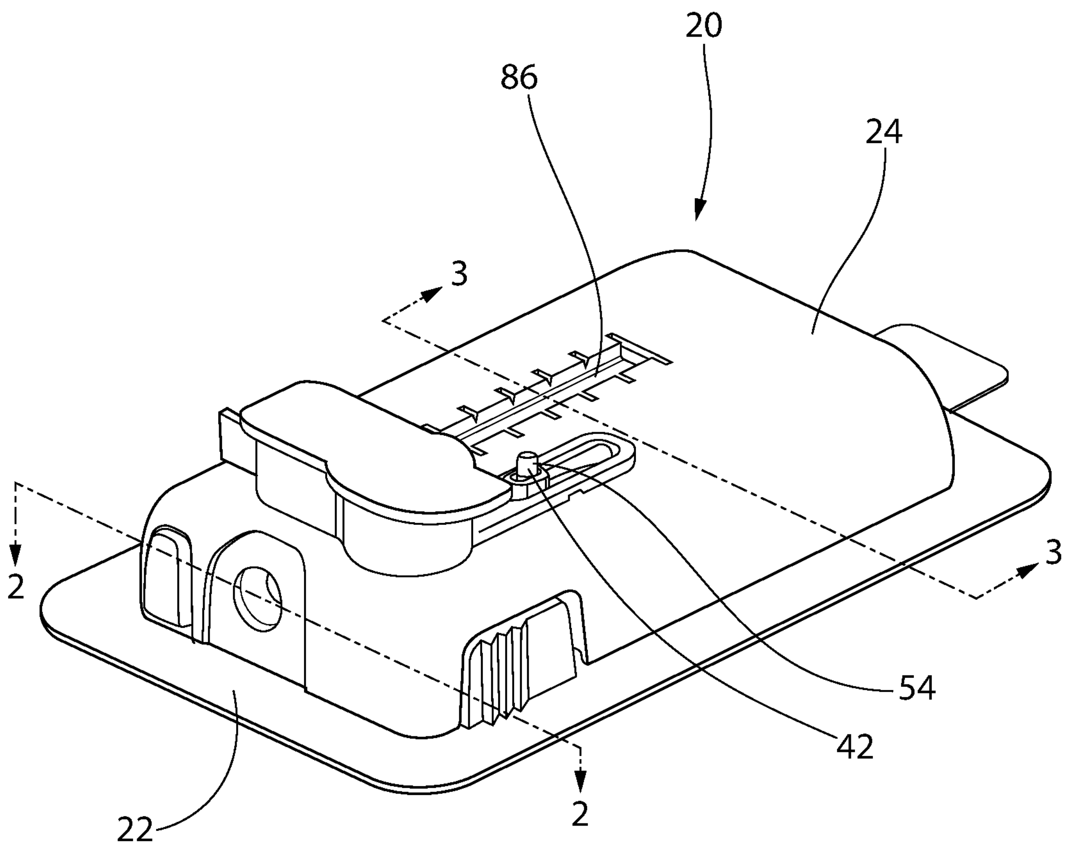
FIG. 1 is a trimetric view of a delivery device in accordance with an exemplary embodiment of the present invention.

Referring to the drawings in detail, wherein like reference numerals indicate like elements throughout, there is shown in FIGS. 1-15 a delivery device, generally designated 20, in accordance with an exemplary embodiment of the present invention. The delivery device 20 may be coupled to a user's skin to deliver a substance to a user such as a drug or medicament. The delivery device 20 may be configured to deliver medicament to a user after a time delay as explained in greater detail below. The delivery device 20 may be configured to deliver a medicament subcutaneously to a user after a delay of a selected or predetermined time period. The delivery device 20 may include a patch 22 which couples the delivery device 20 to a user's skin. The patch 22 may be an adhesive patch that self-adheres to the user's skin. The delivery device 20 may include a housing 24 coupled to the patch 22.

In one embodiment, the delivery device 20 is a discrete ambulatory insulin delivery pump. Delivery device 20 may be single use, disposable and incapable of reuse. The delivery device 20 may provide therapeutic capability in a small, single use, disposable package and at least some portions can be produced using high volume manufacturing fabrication (e.g., injection molding) and assembly processes, allowing for low cost of goods. Embodiments of the delivery device 20 can be used for a broad range of applications, including, but not limited to, clinical applications (e.g., administration of medicaments, etc.) and biomedical research (e.g., microinjection into cells, nuclear or organelle transplantation, isolation of single cells or hybridomas, etc.).

In one embodiment, delivery device 20 is a device for dispensing, delivering, or administering fluid or agent to the user or patient. The fluid may be a low viscosity gel agent and or a therapeutic agent. In one embodiment, the delivery device 20 is configured to deliver Neulasta® (pegfilgrastim) to a user to stimulate the production of white blood cells in chemotherapy patients. Other drugs that require delayed timing include chemotherapy agents, hypertension treatments delivered while sleeping, anti-depressives and pain medication. In one embodiment, the fluid is an analgesic agent. In one embodiment, the fluid is insulin of any type. In other embodiments, the fluid may be, but is not limited to, opiates and/or other palliatives or analgesics, hormones, psychotropic therapeutic compositions, or any other drug or chemical whose continuous dosing, with or without a time delay, is desirable or efficacious for use in treating patients. Single fluids and combinations of two or more fluids (admixed or co-administered) may be delivered using delivery device 20. As used herein "patients" or "user" can be human or non-human animals; the use of delivery device 20 is not confined solely to human medicine, but can be equally applied to veterinarian medicine.

The delivery device 20 may dispense the fluid over a sustained period of time (i.e., basal delivery). In one embodiment, the fluid delivery rate is continuously or near continuously delivered to the user over the sustained period of time. As explained in greater detail below, the delivery device 20 may dispense the fluid over a sustained period of time but the delivery may not begin until after a selected or predetermined time delay. A time delay may allow a caregiver to administer an initial dose of medicament to a patient and attach the delivery device 20 such that a second dose of medicament is delivered to the patient on a selected schedule.

Figure 2:
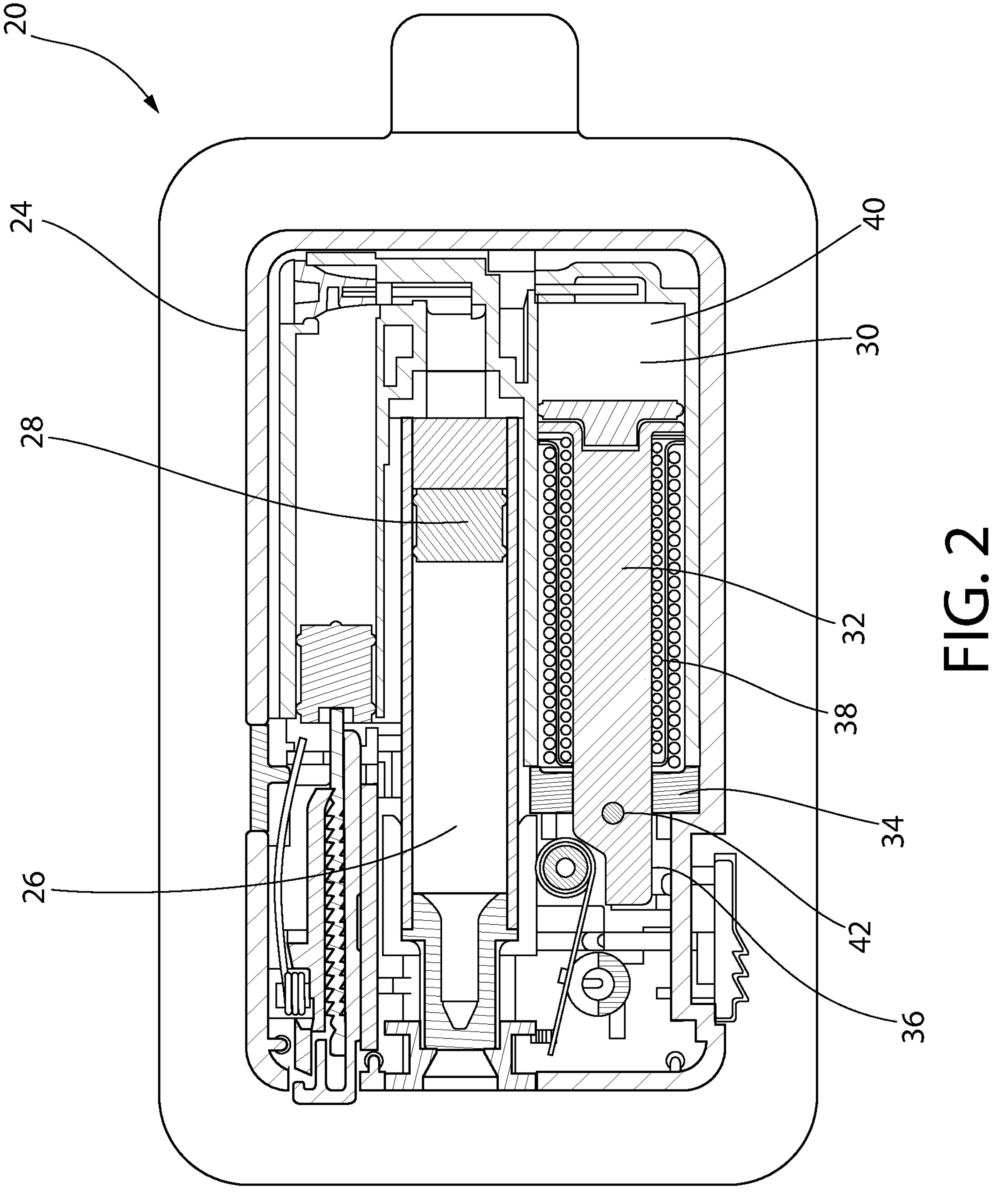
FIG. 2 is a top cross sectional view of the delivery device shown in FIG. 1 taken along a plane, the location and direction being indicated by line 2-2.
Figure 3:
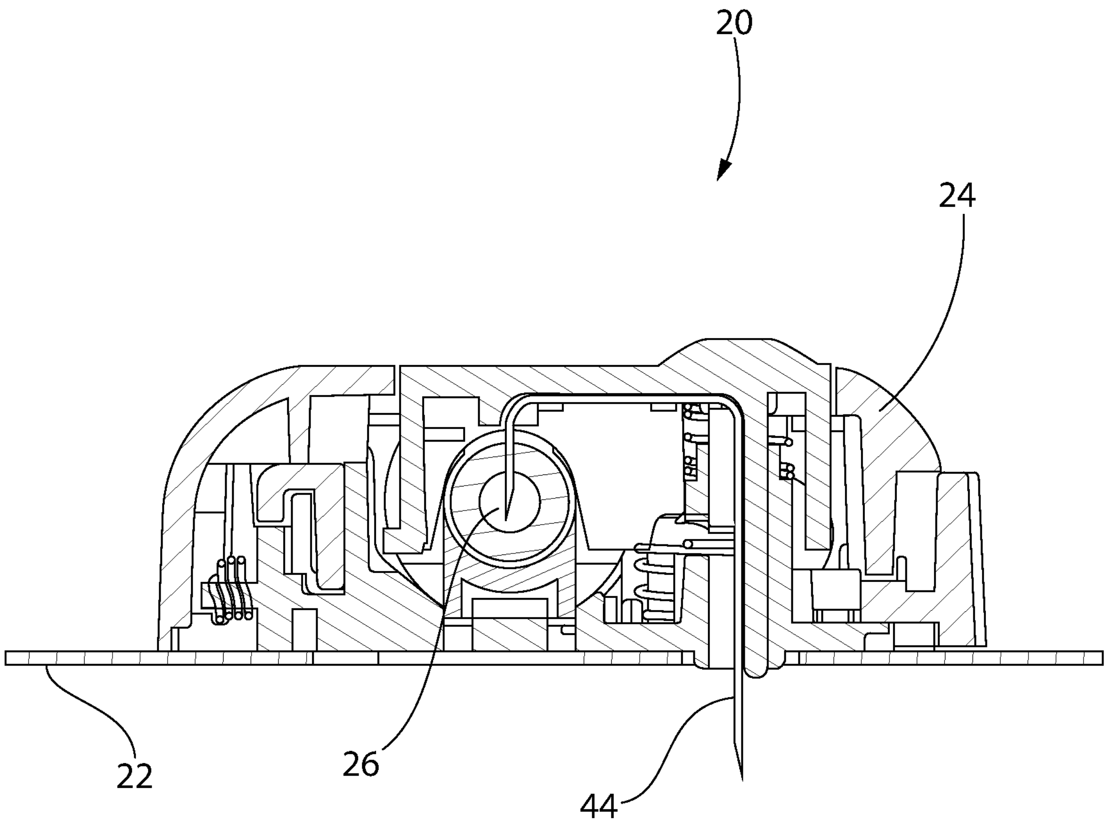
FIG. 3 is a front cross sectional view of the delivery device shown in FIG. 1 taken along a plane, the location and direction being indicated by line 3-3.

Referring to FIG. 2, the delivery device 20 may include a medicament chamber 26 within the housing 24. A plunger 28 may be positioned in the medicament chamber 26. The plunger 28 may be moveable within the medicament chamber 26 to expel medicament from the medicament chamber 26 as explained in greater detail below. In one embodiment, the plunger 28 is moved relative to the medicament chamber 26 by fluid pressure (e.g., hydraulic fluid). In another embodiment, the plunger 28 is moved directly or indirectly by a biasing element (e.g., a spring) or gas pressure.

The delivery device 20 may include a second chamber 30 containing fluid. A second plunger 32 may be positioned in the second chamber 30. The second chamber 30 may be fluidly connected to the medicament chamber 26 by a channel. The second plunger 32 may be moveable relative to the second chamber 30 to expel the fluid from the second chamber 30 through the channel and into the medicament chamber 26. A wall 34 may be positioned at a proximal end 36 of the second chamber 30. The wall 34 may be fixed relative to the second chamber 30. A biasing element 38 may be positioned between the fixed wall 34 and a portion of the plunger 32. The biasing element 38 (e.g., a spring or compressed gas) may move from a compressed state to a decompressed state thereby moving the plunger 32 toward a distal end 40 of the second chamber.

A catch such as a pin 42 may be coupled to the second plunger 32 to prevent the second plunger from moving relative to the second chamber 30. In one embodiment, the pin 42 has a circular cross section. In one embodiment, the pin 42 has a non-circular cross section such as square. The pin 42 may extend through, or be coupled to, the housing 24 such that the pin 42 contacts the housing thereby preventing movement of the second plunger 32 when the pin is in a first pin position. The pin 42 may be movable relative to the second plunger 32. The pin 42 may be moveable from the first pin position where the pin 42 prevents movement of the second plunger 32 to a second pin position where the pin 42 allows movement of the second plunger 32. Decoupling the pin 42 from the second plunger 32 may allow the second plunger to move relative to the second chamber 30. The pin 42 could also, or alternatively, be coupled to the plunger 28 of the medicament chamber 26. In one embodiment, the second plunger 32 may include a recess or hole to receive the pin 42. In another embodiment, the second plunger 32 may include a shoulder or protrusion to engage the pin 42 such that the second plunger 32 is restrained from moving toward the distal end of the second chamber 30 when the pin 42 is in the first pin position.

The biasing element 38 may move the second plunger 32 toward the distal end 40 of the second chamber 30 when the pin 42 is decoupled from the second plunger 32. The movement of the second plunger 32 relative to the second chamber 30 may expel the fluid from the second chamber 30 through the channel and into the medicament chamber 26. Thus, the biasing element 38 may cause each of the second plunger 32 and the plunger 28 to move relative to the second chamber 30 and the medicament chamber 26, respectively. The plunger 28 may separate the medicament from the fluid in the medicament chamber 26 such that as the fluid from the second chamber 30 enters the medicament chamber 26, the medicament is expelled through a needle 44 and into the user (needle 44 best seen in FIG. 3).

The delivery device 20 may include a communication module configured to communicate with a remote device. The communication module may be configured to communicate via a wired connection or wirelessly (e.g., near field communication (NFC), infrared (IR) wireless communication, Bluetooth, or Zigbee). The communication module may communicate with an application on a user's phone or computer. The app may cause the user's phone to provide a signal (e.g. audible or tactile notification) to notify a user when to begin delivery of the medicament from the delivery device 20. The communication module may be coupled to the pin 42 such that removing the communication module when alerted to do so begins the delivery of the medicament. The communication module may transmit a signal to the app that the module was removed at the proper time. A user may input a signal into the app that the delivery device 20 has been coupled to the user and the app may send a second signal after a selected time delay to notify the user to activate the delivery device 20 by removing the pin 42.

The delivery device 20 may include a timer configured to notify a user when to begin the delivery of the medicament and/or when to remove the delivery device 20. The timer may include an alarm to provide an audio, visual, and/or tactile signal to a user to activate the delivery device 20 to deliver the medicament. The timer may be connected to the pin 42 such that removing the timer from the delivery device 20 activates the delivery device. In one embodiment, the timer is an external device that is attached to the delivery device. In one embodiment, the timer is positioned within the housing 24.

Figure 4:
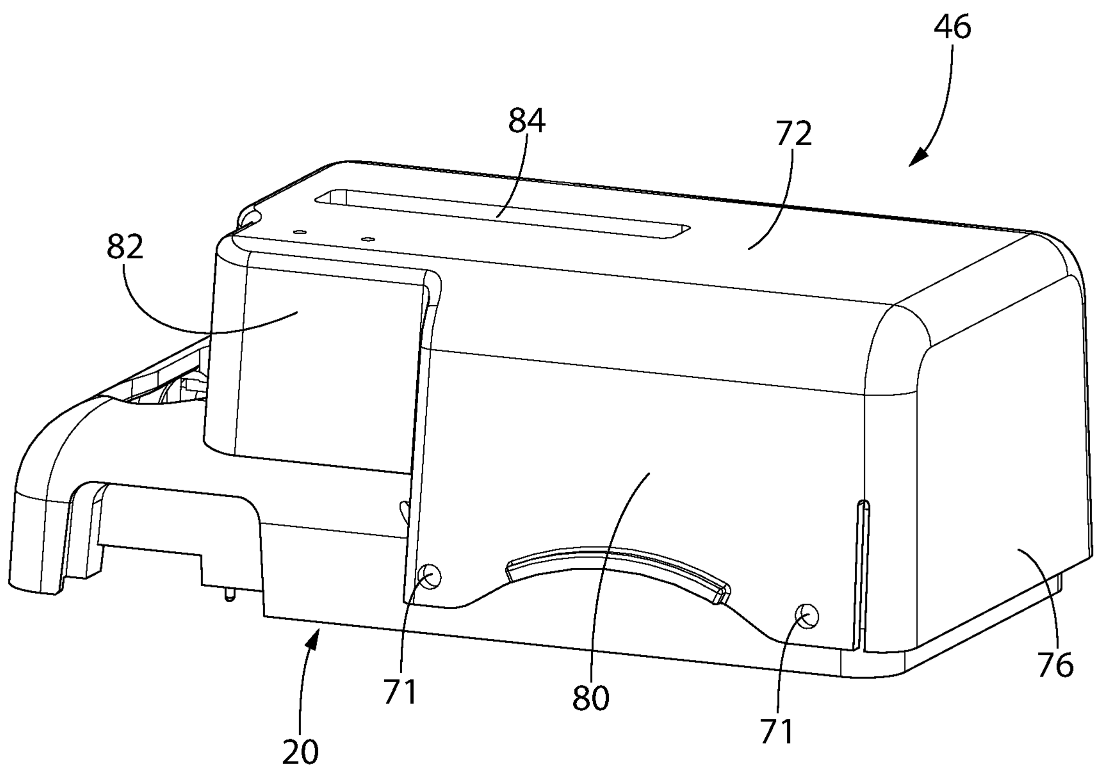
FIG. 4 is a side trimetric view of the delivery device of FIG. 1 with an actuation assembly in accordance with an exemplary embodiment of the present invention attached thereto.

Referring to FIG. 4, an actuation assembly 46 may be coupled to the delivery device 20. Some of the elements are removed from the delivery device 20 as shown in FIG. 4 for ease of discussion. The actuation assembly 46 may be configured to activate the delivery device 20 after a selected time delay. The actuation assembly 46 may be coupled to an existing delivery device 20. In one embodiment, the user of the delivery device 20 connects the actuation assembly 46 with the delivery device 20. In one embodiment, the actuation assembly 46 is coupled to the delivery device 20 during manufacturing so that the user receives the delivery device 20 with actuation assembly 46 already coupled to the delivery device 20. In one embodiment, the actuation assembly 46 is integrally formed with the delivery device 20. In one embodiment, the actuation assembly 46 is removably coupled to the delivery device 20. In one embodiment, the actuation assembly 46 locks onto the delivery device 20 and is not intended to be removed from the delivery device 20.

The actuation assembly 46 may be configured to move the pin 42 from the first pin position (FIG. 8) to the second pin position (FIG. 9) as explained in greater detail below. The actuation assembly 46 may be configured to delay the start of delivery device 20. For example, the delivery device 20 may be attached to the user and the user or the caregiver may start the actuation assembly 46 so that the delivery device 20 is not activated until after a predetermined time delay as set by the actuation assembly 46. The time delay may be any desired amount of time. The time delay may be about 1 second, about 5 seconds, about 10 seconds, about 30 seconds, about 1 minute, about 5 minutes, about 15 minutes, about 30 minutes, about 45 minutes, about 1 hour, about 3 hours, about 5 hours, about 10 hours, about 15 hours, about 18.5 hours, about 20 hours, about 24 hours, about 36 hours, or about 48 hours.

Referring to FIGS. 4-7, the actuation assembly 46 may include an adapter 48 (FIG. 7) configured to engage the pin 42 (see FIG. 2). The adapter 48 may include an internal opening 50 configured to receive at least a portion of the pin 42. One or more flanges 52 may extend into the internal opening 50. The flanges 52 may engage the pin 42 when the pin 42 is in the internal opening 50. The pin 42 may include a head 54 and a body 57. A neck 59 may be formed between the head 54 and the body 57 of the pin 42. The neck 59 may have a smaller diameter than the head 54 and/or the body 57 such that the flanges 52 engage the neck 59 when the head 54 is within the internal opening 50. The flanges 52 may be resilient such that the flanges deflect as the head 54 enters the internal opening 50 and contacts the flanges 52. The flanges 52 may return to their undeflected state when the flanges 52 are adjacent the neck 59. In some embodiments, the adapter 48 includes a magnet and the pin 42 comprises a magnetic or ferrous material such that the adapter 48 is magnetically coupled to the pin 42.

Figure 5:
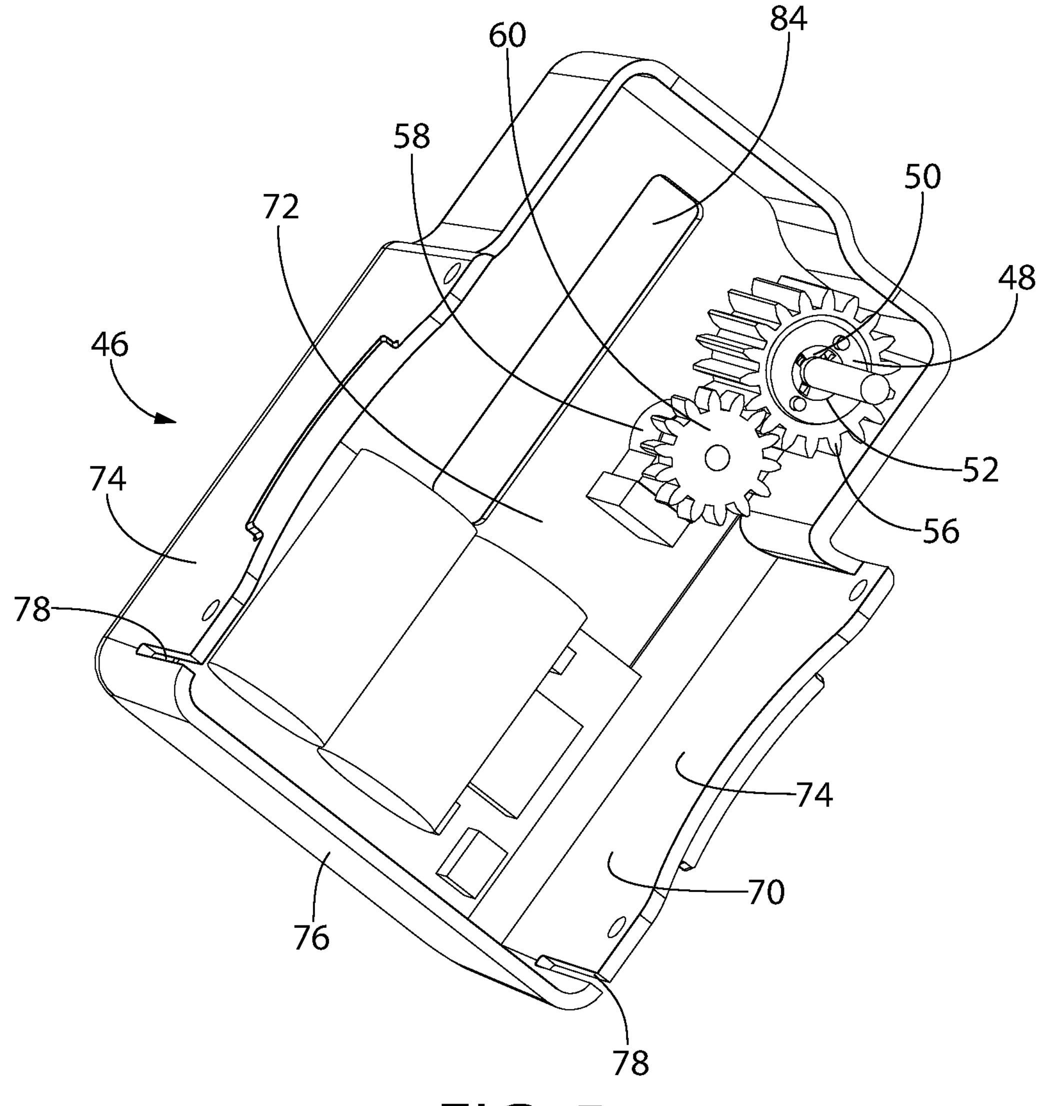
FIG. 5 is a bottom trimetric view of the actuation assembly of FIG. 4.

Referring to FIG. 5, the actuation assembly 46 may include a gear 56. The gear 56 may be configured to rotate relative to the actuation assembly 46. The actuation assembly may include an activator 58 configured to rotate the gear 56. In one embodiment, the activator 58 is a DC motor such as Precision Microdrives model 103-100 or model 124-002. In another embodiment, the activator 58 is a pull string, a turnable knob, or a crank handle. In one embodiment, the activator 58 is coupled to a drive gear 60 which meshes with the gear 56 such that the activator 58 rotates the drive gear 60 which causes the gear 56 to rotate. In another embodiment, the activator 58 is coupled to the gear 56 such that the motor rotates gear 56.

Figure 6:
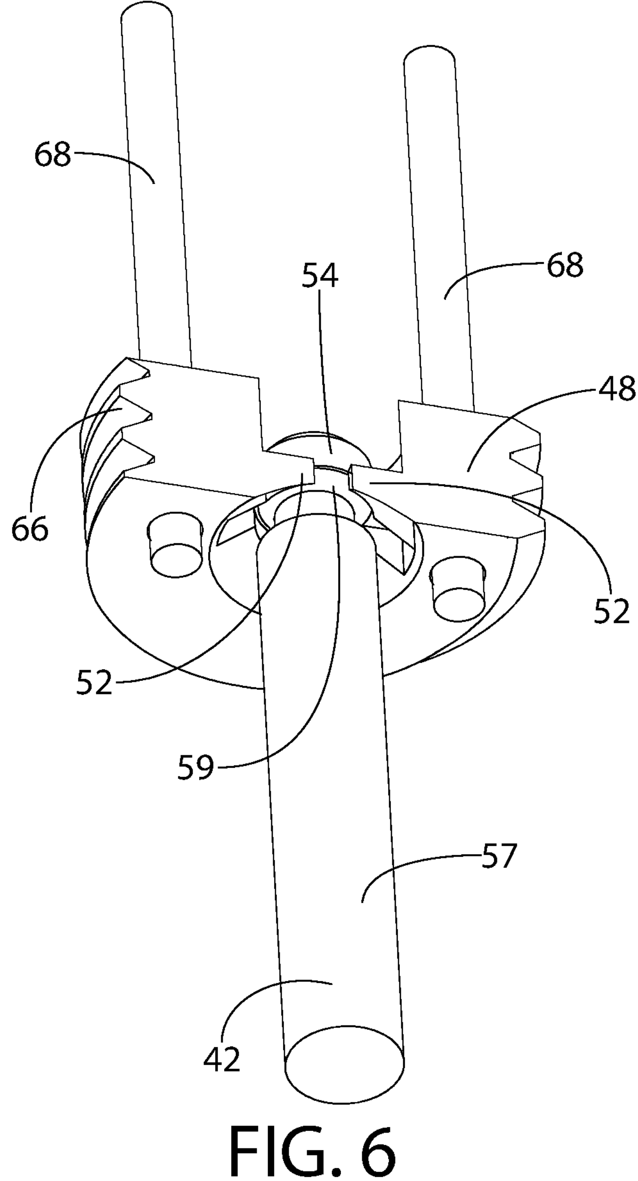
FIG. 6 is a sectional trimetric view of an interface adapter component of FIG. 4.
Figure 7:
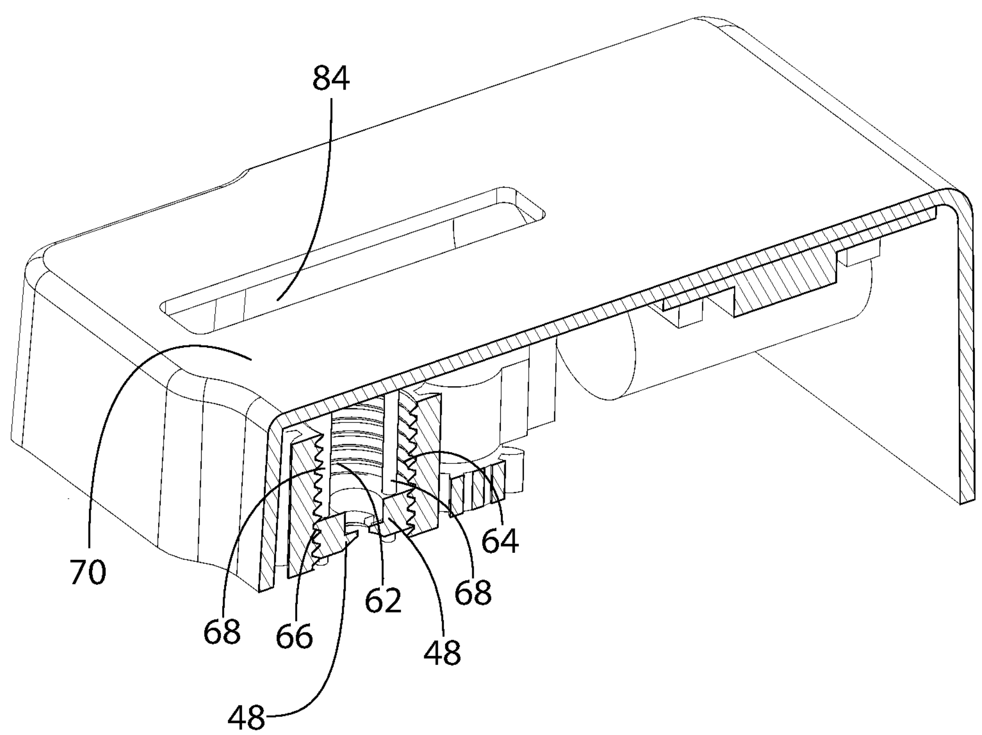
FIG. 7 is a top, side, sectional trimetric view of the actuation assembly of FIG. 4.

Referring to FIGS. 5-7, the gear 56 may include an internal opening 62 configured to receive the adapter 48. The adapter 48 may move relative to the gear 56 as the gear rotates. The internal opening 62 may be defined by a threaded perimeter wall 64. The adapter 48 may include an external thread 66 configured to mesh with the threaded perimeter wall 64 such that relative rotation between the gear 56 and the adapter 48 causes translation of the adapter 48 relative to the gear 56. The actuation assembly 46 may include one or more posts 68. The posts 68 may be fixed to an actuation assembly housing 70. The adapter 48 may include openings to slidingly receive the posts 68 such that the adapter 48 can translate relative to the posts 68 and the gear 56. The posts 68 may rotatingly fix the adapter 48 relative to the actuation assembly 46 and/or the gear 56 as the gear 56 rotates such that the threaded engagement between the adapter 48 and the gear 56 causes the adapter 48 to translate as the gear rotates.

Referring to FIGS. 4-5, the actuation assembly housing 70 may include a top wall 72 with sidewalls 74 extending away from the top wall 72. A rear wall 76 may be coupled to the sidewalls 74. A relief 78 may be formed at the transition between the sidewall 74 and the rear wall 76 such that the sidewall 74 can flex independently from the rear wall 76 as the housing 70 is positioned on the delivery device 20. The sidewalls 74 may include a first portion 80 adjacent the rear wall 76 and a second portion 82 adjacent the first portion 80. The first portion 80 may extend away from the top wall 72 further than the second portion 82. The length of the first portion 80 and the rear wall 76 may help align the actuation assembly 46 on the delivery device 20 as the actuation assembly 46 is coupled to the delivery device 20. Aligning the actuation assembly 46 on the delivery device 20 may ensure that the adapter 48 receives a portion of the pin 42 when the actuation assembly 46 is coupled to the delivery device 20. The sidewalls 74 may include features 71 (FIG. 4) to secure the housing 70 to the delivery device 20. The features 71 may engage housing features 73 (best seen in FIG. 11). In one embodiment, the sidewall features 71 may be a protrusion and the housing feature 73 may be a recess configured to at least temporarily receive the protrusion. In another embodiment, the sidewall feature 71 is a recess and the housing feature 73 is a protrusion. In another embodiment, feature 71 and feature 73 are both holes configured to receive a dowel, pin, screw, or fastener. In yet another embodiment, feature 71 and feature 73 form a hook and loop fastener (e.g., Velcro) or are magnets. Projections (not shown) may be formed at the bottom edges of the sidewalls 80 to make it easier to grip the housing for removal. The top wall 72 may include a window 84. The window 84 may allow a user to observe a dosage indicator 86 in the delivery device 20 (FIG. 1) or the contents of the delivery device medicament chamber 26.

Figure 8:
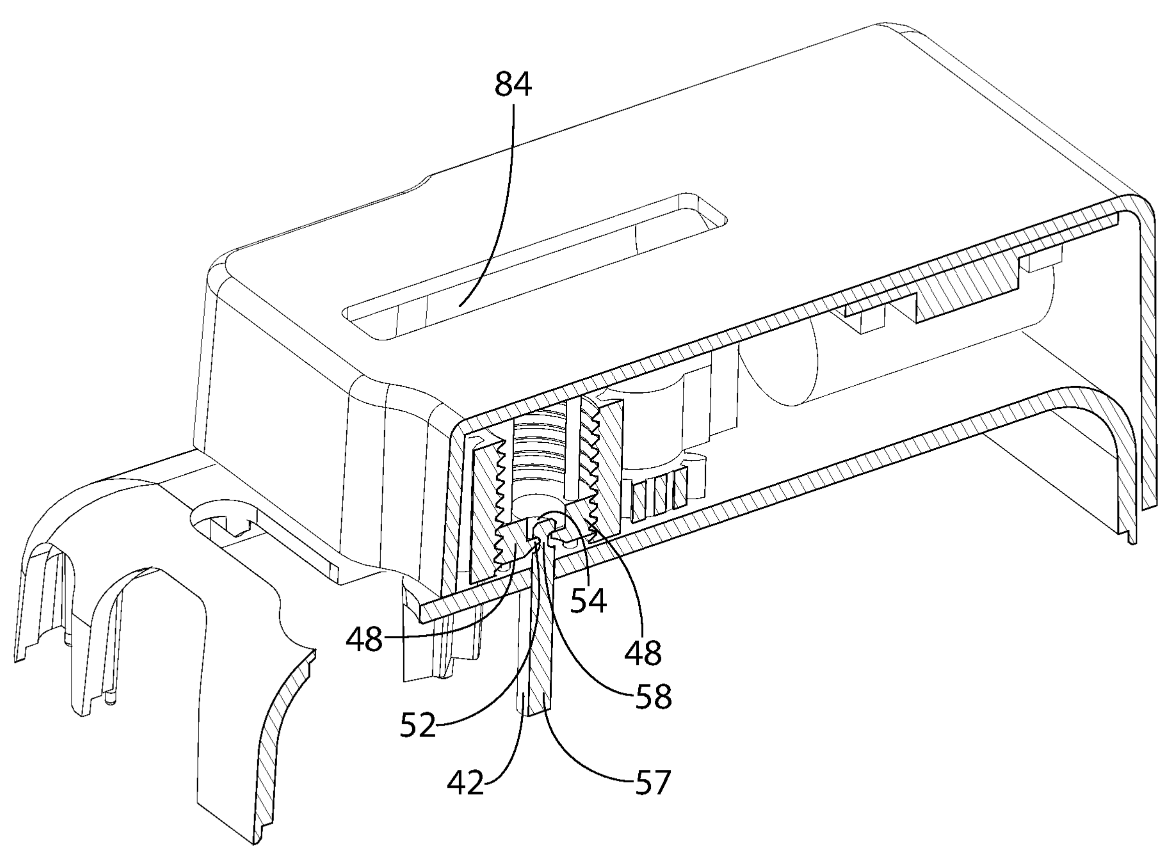
FIG. 8 is a top, side, sectional trimetric view of the delivery device and actuation assembly of FIG. 4.
Figure 9:
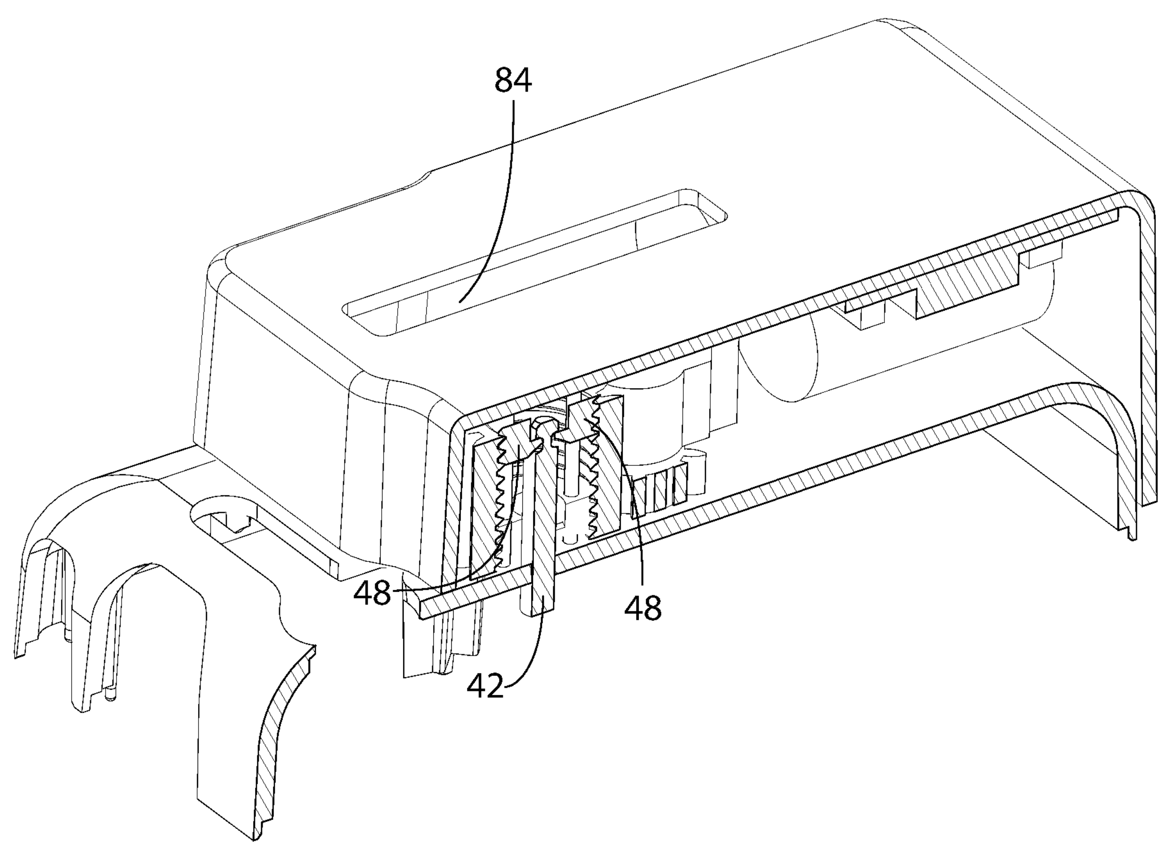
FIG. 9 is a top, side, sectional trimetric view of the delivery device and actuation assembly of FIG. 4.

Referring to FIGS. 8-9, the adapter 48 may move from the first adapter position (FIG. 8) to the second adapter position (FIG. 9) as the gear 56 rotates. The flanges 52 may contact the head 54 of the pin 42 and move the pin 42 from the first pin position to the second pin position as the adapter 48 is moved from the first pin position to the second pin position. The biasing element 38 (FIG. 2) may move the second plunger 32 after the pin 42 is moved to the second pin position. Fluid may be transferred from the second chamber 30 to the medicament chamber 26 as the second plunger 32 is moved by the biasing element 38 thereby moving the plunger 28 to move. The medicament may be dispensed from the medicament chamber 26 as plunger 28 moves. In some embodiments, the second plunger 32 does not move until the adapter 48 or activator 58 has stopped moving. In some embodiments, the delivery device includes discrete steps of movement of the activator 58 and then movement of the second plunger 28.

Figure 10:
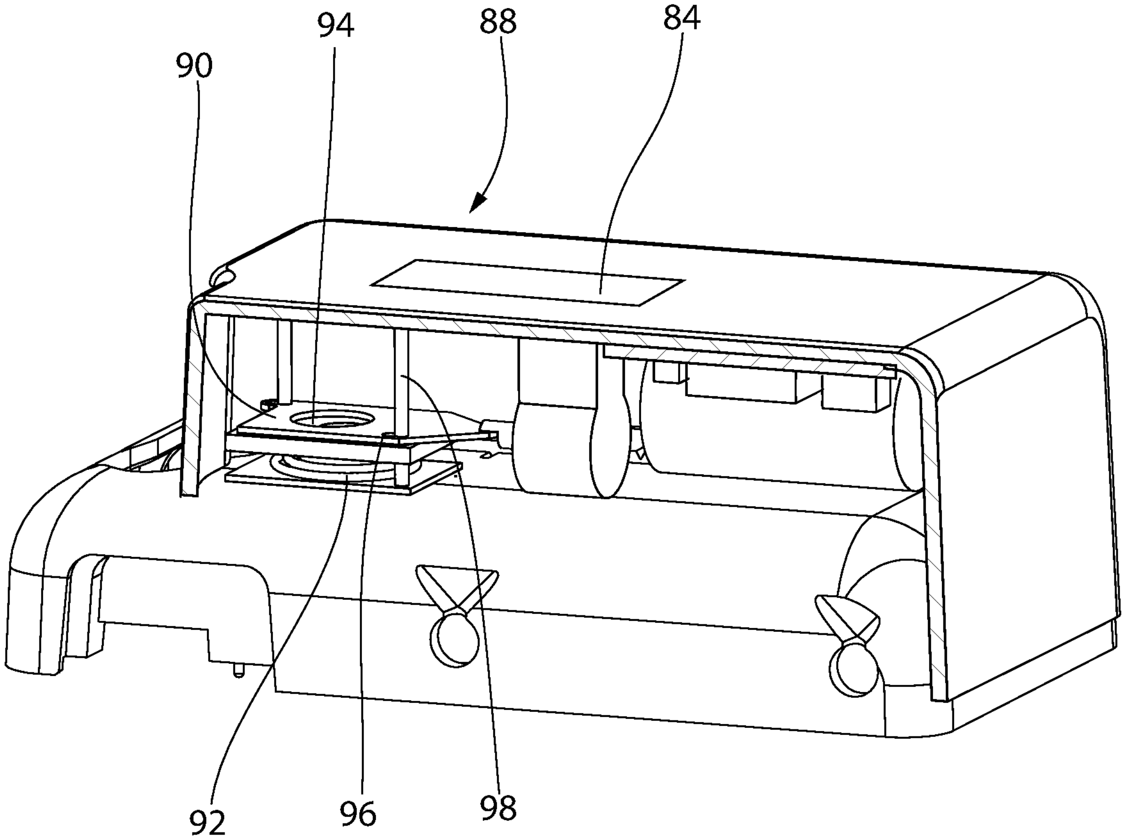
FIG. 10 is a side trimetric view of the delivery device of FIG. 1 with an actuation assembly in accordance with another exemplary embodiment of the present invention attached thereto.
Figure 11:
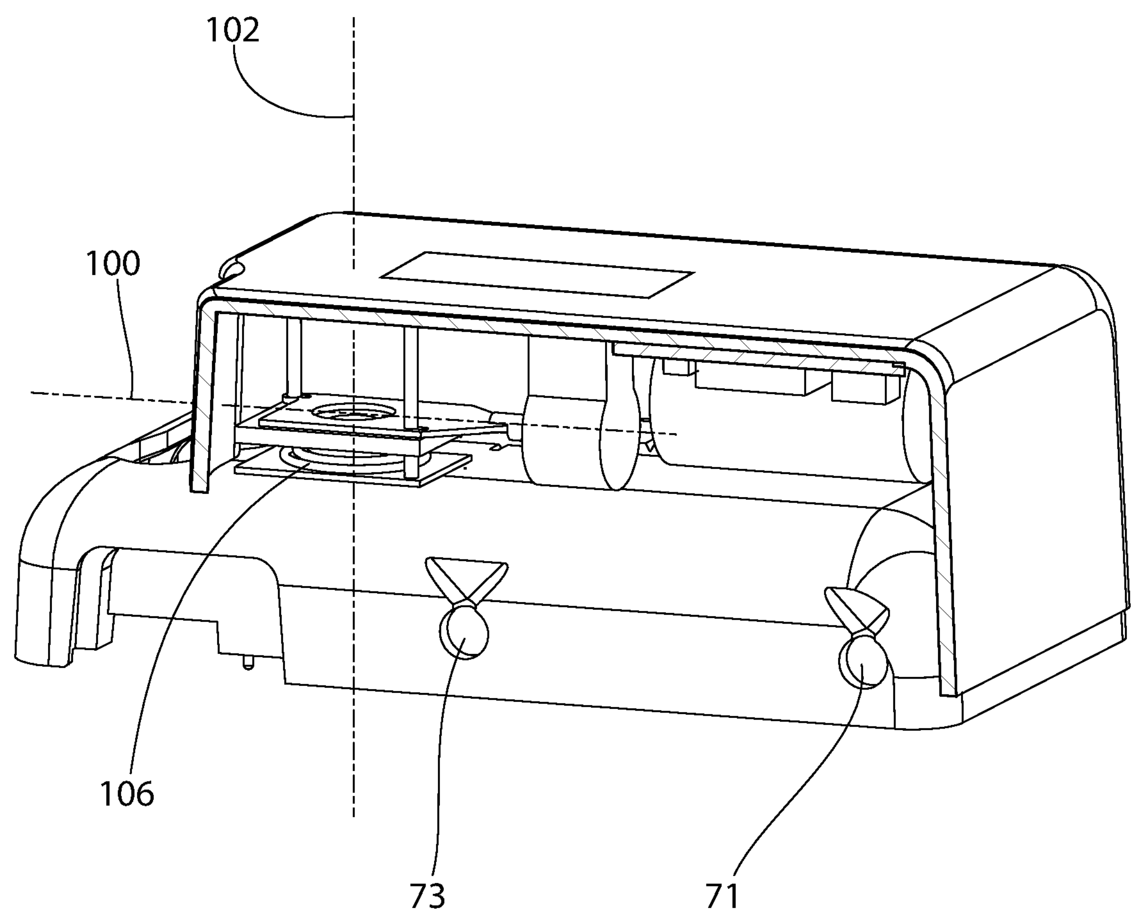
FIG. 11 is a side trimetric view of the delivery device and actuation assembly of FIG. 10.
Figure 12:
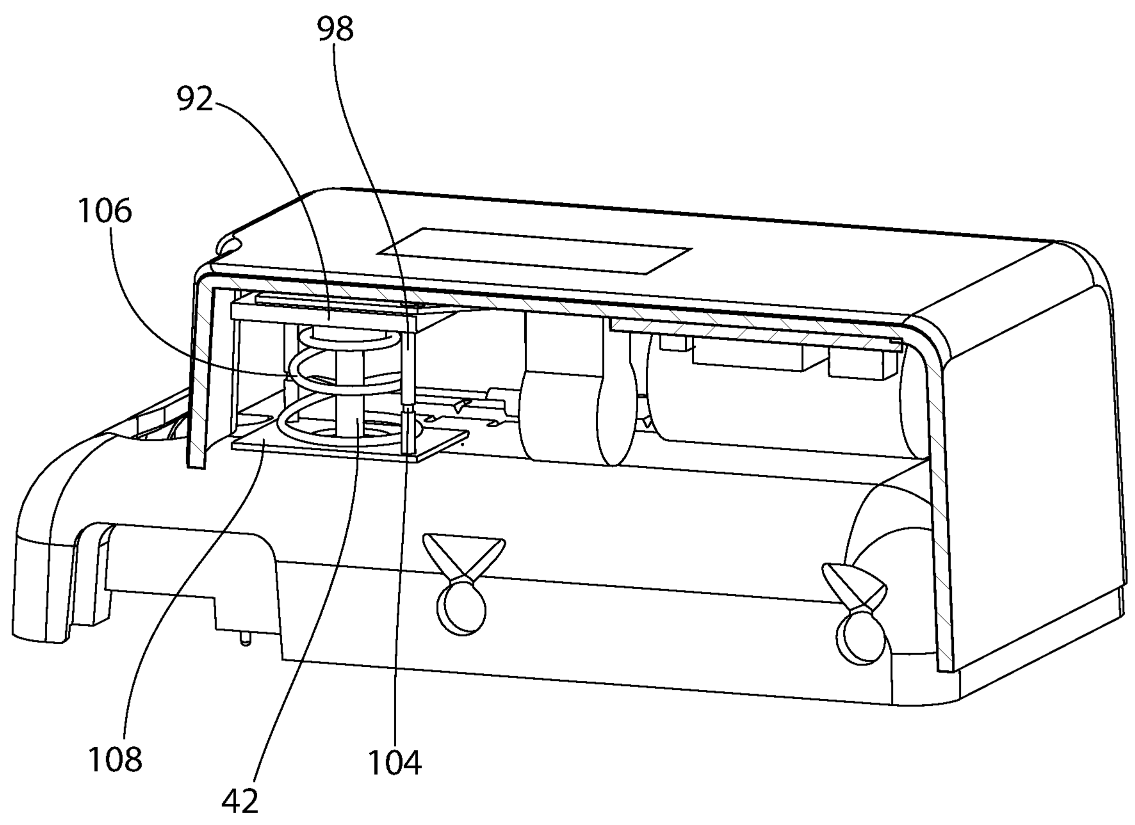
FIG. 12 is a side trimetric view of the delivery device and actuation assembly of FIG. 10.
Figure 13:
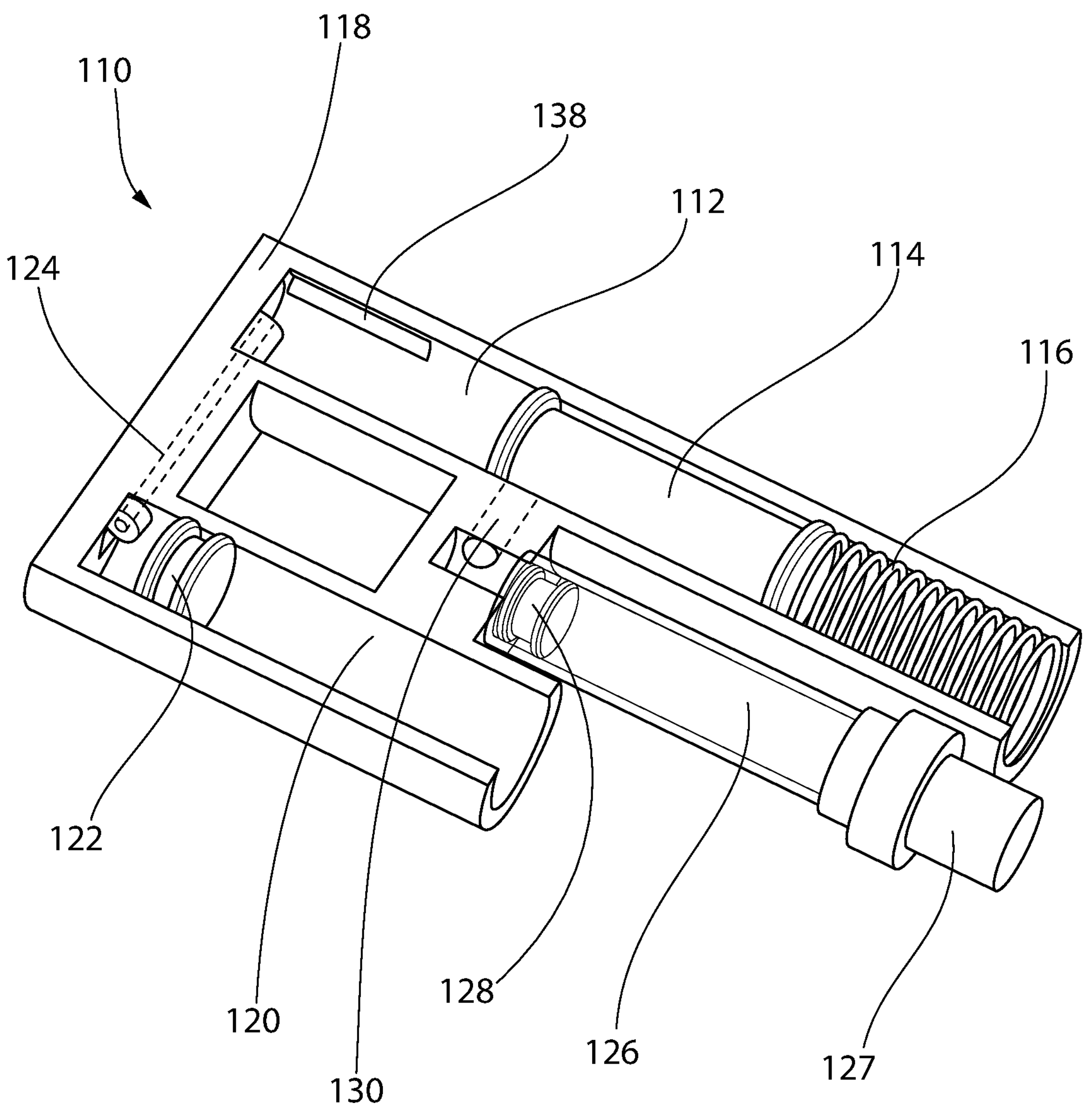
FIG. 13 is a top, side trimetric view of a delivery device in accordance with another embodiment of the present invention.
Figure 14:
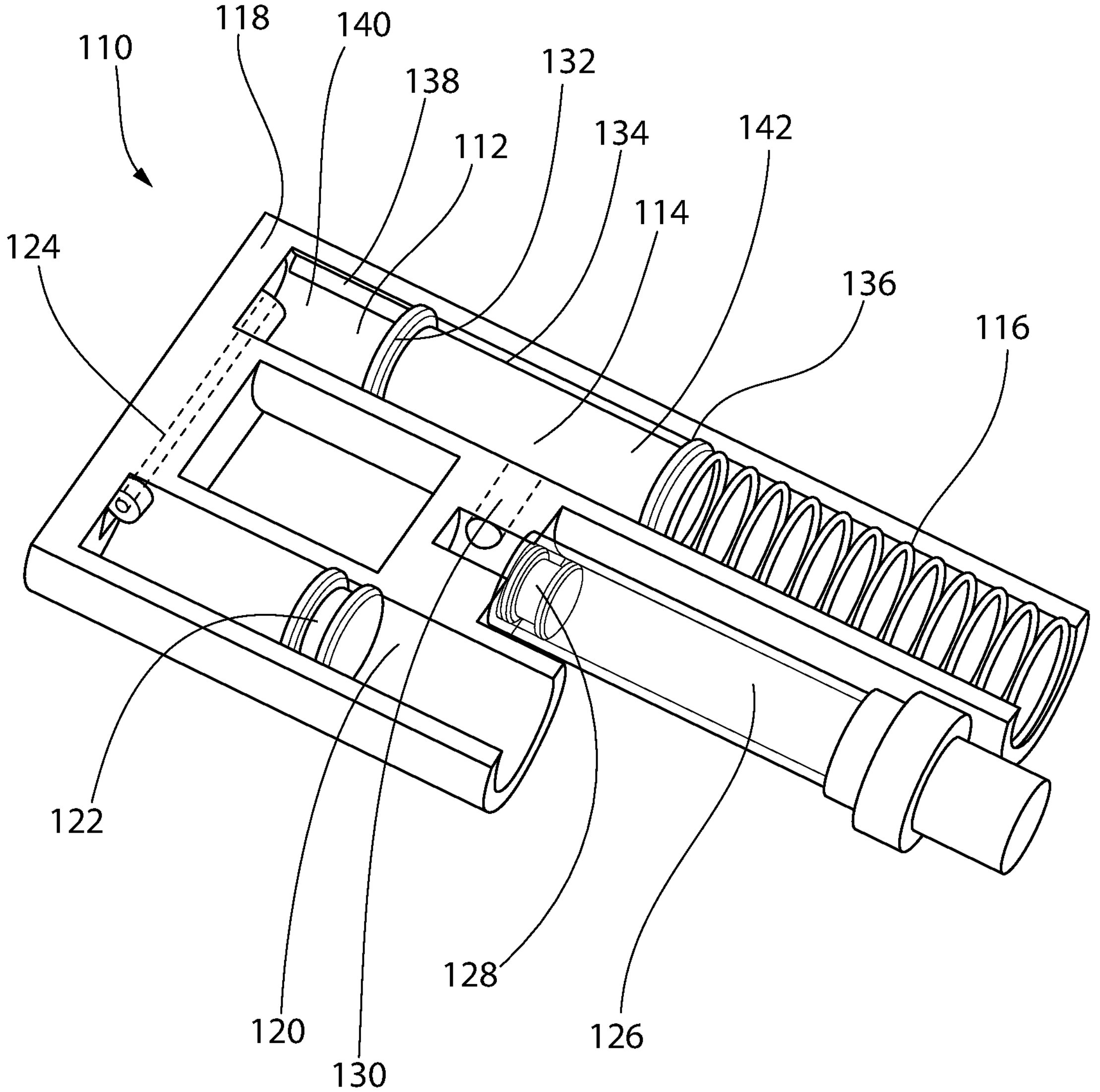
FIG. 14 is a top, side trimetric view of the delivery device of FIG. 13.
Figure 15:
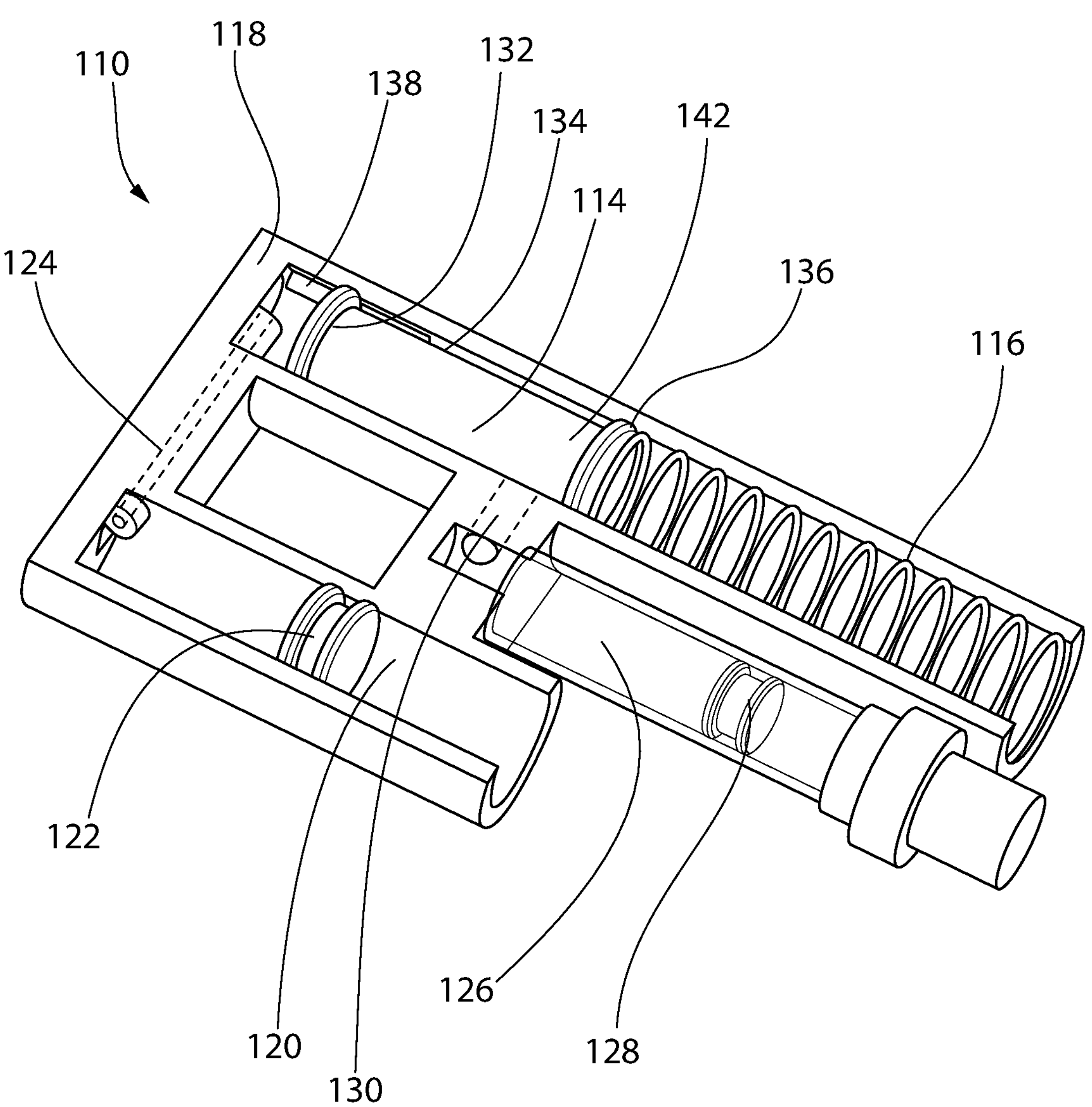
FIG. 15 is a top, side trimetric view of the delivery device of FIG. 13.

Referring to FIGS. 10-12, there is shown a second embodiment of the actuation assembly, generally designated 88. The actuation assembly 88 may be similar to the first embodiment of the actuation assembly 46, but one difference is that the actuation assembly 88 does not include a gear 56.

The actuation assembly 88 may include an engagement member 90 coupled to an adapter 92. The adapter 92 may include the internal opening 50 and flanges 52 to engage the pin 42 as previously described. The engagement member 90 may be moveable relative to the adapter 92 from a first engagement member position (FIG. 11) to a second engagement member position (FIG. 12). In one embodiment, the engagement member 90 is slidably coupled to the adapter 92 such that the engagement member 90 is slidable along a first axis 100 relative to the adapter 92. The engagement member 90 may include an opening 94 to receive the pin head 54 when the pin 42 is engaged by the adapter 92.

The engagement member 90 may be moveable along a second axis 102 relative to the actuation assembly 88 (FIGS. 11-12). The engagement member may include an aperture 96 configured to receive a post 98. The post 98 may include a catch 104 (FIG. 12) configured to prevent movement of the engagement member 92 along the second axis 102. The catch 104 may be a notch or a portion of the post 98 having a reduced thickness compared to an adjacent portion of the post 98. The post 98 may include a shoulder at the catch 104 such that the catch 104 engages a surface or edge of the engagement member 94 to prevent the engagement member from moving along the second axis 102 when the engagement member is in the first engagement member position. In one embodiment, the second axis 102 is orthogonal to the first axis 100. In another embodiment, the second axis 102 is oblique to the first axis 100.

The engagement member 90 may be moveable along the first axis 100 from the first engagement member position where the catch 104 prevents movement of the engagement member 90 along the second axis 102 to the second engagement member position where the engagement member can move along the second axis 102. In one embodiment, the catch 104 extends around the perimeter of the post 98. In another embodiment, the catch 104 is formed on only a portion of the perimeter of the post 98 to prevent accidental engagement between the catch 104 and the engagement member 90 when the engagement member is moved to the second position. In still another embodiment, one side of the sidewall of the aperture 96 is thicker than another side such that the catch 104 can only engage the engagement member 90 when the engagement member is in the first engagement member position.

Referring to FIGS. 11-12, the actuation assembly 88 may include a biasing element 106 configured to urge the adapter 92 toward the second adapter position. In one embodiment, the biasing element 106 is a spring. The actuation assembly 88 may include a base plate 108 and the biasing element 106 may be coupled to the base plate 108 and the adapter 92. The biasing element 106 may move the adapter 92 to the second adapter position (FIG. 12) when the engagement member 90 disengages from the catch 104. The adapter 92 may move the pin 42 from the first pin position to the second pin position as the adapter 92 moves from the first adapter position (FIG. 11) to the second adapter position (FIG. 12). The actuation assembly 88 may include an actuator (not shown) configured to move the engagement member from the first engagement member position to the second engagement member position. In one embodiment, the actuator could be the gear 56 and activator 58 such that rotation of the gear 56 causes the engagement member 90 to move along the first axis 100. In another embodiment, a user may manually move the engagement member either by manually engaging the engagement member or engaging an element coupled to the engagement member.

Rather than have an external device control the activation of the delivery device 20, the delay mechanism may be internal to the housing 24. For example, referring to FIGS. 13-15, there is shown a second embodiment of a delivery device, generally designated 110. The delivery device 110 is similar to the delivery device 20 previously described and some of the features have been omitted in FIGS. 13-15 for ease of discussion. The delivery device 110 may be configured to deliver medicament to a user upon activation of the delivery device 110 and after a pre-determined time delay. One or more features of the delivery device 110 may be selected to provide a desired time delay, as explained in greater detail below.

The delivery device 110 may include a first chamber 112 with a first plunger 114 in the first chamber 112. The first plunger 114 may be moveable relative to the first chamber 112. The first chamber may include a biasing element 116 configured to urge the first plunger 114 toward a distal end 118 of the first chamber 112. The first plunger 114 may be at least temporarily held in place by the pin 42 as previously described and the pin may be moved by one of the actuation assemblies 46, 88 as previously described. The first chamber 112 may be configured to receive a fluid (e.g., hydraulic fluid).

The delivery device 110 may include a second chamber 120. The second chamber may be sealed with a membrane. The membrane (not shown) could be a flexible membrane, an expandable membrane, or a gas permeable membrane. The delivery device 110 may include a second plunger 122 in the second chamber 120. The second plunger 122 may fluidly seal the second chamber 120. The flexible membrane or second plunger 122 may be configured to move relative to the second chamber 120 when the first plunger 114 moves relative to the first chamber 112. The second chamber 120 may be configured to receive the fluid from the first chamber. A first passage 124 may fluidly connect the first chamber 112 to the second chamber 120. Fluid may be transferred from the first chamber 112 through the first passage 124 and into the second chamber 120 as the first piston 114 moves relative to the first chamber 112. The second piston 122 may move relative to the second chamber 120 as the fluid enters the second chamber 120. In another embodiment, the second chamber 120 is sealed with a gas permeable membrane that allows air to escape as the fluid is transferred from the first chamber 112 but prevents fluid from escaping.

The delivery device 110 may include a third chamber 126. A third plunger 128 may be movably positioned in the third chamber 126. The third chamber 126 may be adapted to receive medicament. The medicament from the third chamber 126 may be delivered through a needle to a user when the third plunger 128 moves relative to the third chamber 126 as previously described. The third chamber 126 may include an end cap 127 configured to be fluidly coupled to the needle 44 and the third chamber 126 such that the medicament is transferred from the third chamber 126 through the needle and to a user. The third chamber 126 may be configured to expel medicament from the third chamber 126 when the first plunger 114 moves relative to the first chamber 112. The third plunger 128 may fluidly seal the third chamber 126 such that the medicament in the third chamber 126 is separated from the fluid entering the third chamber 126.

A second passage 130 may fluidly connect the first chamber 112 to the third chamber 126. At least a portion of the fluid from the first chamber 112 may flow into the third chamber 126 as the first plunger 114 moves relative to the first chamber 112. In one embodiment, the fluid flows from the first chamber 112 into the second chamber 120 before the fluid flows from the first chamber 112 into the third chamber 126. In one embodiment, a diameter of the first passage 124 is smaller than a diameter of the second passage 130. The length of the first passage 124 may be greater than the length of the second passage 130. The length of the first passage 124 may exceed the length of the second passage 130 by a length equal to or greater than a diameter of the third chamber 126.

The first plunger 114 may include a first collar 132 configured to fluidly seal the first chamber 112. The first collar 132 may have an outer diameter substantially similar to, or slightly larger than, the diameter of the first chamber

112 such that fluid is prevented from flowing past the first collar 132. The first plunger 114 may include a body 134 adjacent the first collar 132. The body 134 may have a diameter smaller than the first collar 132 and the first chamber 112 such that fluid can flow around the body 134. The first plunger 114 may include a second collar 136 having a diameter substantially similar to or the same as the first collar 132.

The first chamber 112 may include a distal portion 140 between the distal end 118 of the first chamber 112 and the first collar 132. A proximal portion 142 of the first chamber 112 may be between the first collar 132 and the second collar 136 of the first plunger 114. The first chamber 112 may include a bypass 138. The bypass 138 may be a recess in a sidewall of the first chamber 112 such that fluid can flow from the distal portion 140 through the bypass 138 and into the proximal portion 142. The fluid may flow from the proximal portion 142 through the second passage 130 and into the third chamber 126. However, in some embodiments, the bypass 138 does not extend the entire length of the first chamber 112 such that the fluid does not flow from the distal portion 140 to the proximal portion 142 until the first collar 132 is moved adjacent the bypass 138. Thus, the fluid may flow into the second chamber 120 before fluid flows into the third chamber 126. The fluid may flow into the second chamber 120 and the third chamber 126 simultaneously once the fluid has begun flowing into the third chamber 126. The time necessary for the first plunger 114 to move such that the first collar 132 is adjacent the bypass 138 may be the selected time delay. The spring constant of the biasing element 116, the friction between the first plunger 114 and the first chamber 112, and the length of the first chamber 112 may be selected to achieve the selected time delay.

The length, diameter, and/or material of the first passage 124 and the second passage 130 and the viscosity of the hydraulic fluid in the first chamber 112 may be selected to vary the volumetric flow rate through each of the first passage 124 and the second passage 130. The flow rate through the first passage 124 may be slower than the flow rate through the second passage 130. The flow rate through the first passage 124 may at least partially influence the movement rate of the first piston 114 relative to the first chamber 112. For example, a shorter first passage 124 may provide a greater flow rate of the fluid through the first passage than a longer first passage 124. A relatively larger diameter first passage 124 may allow a greater flow rate of the fluid through the first passage than a relatively smaller diameter first passage 124. The flow rate through the first passage 124 may influence a time delay from a time the first plunger 114 begins to move relative to the first chamber 112 until the fluid flows into the third chamber 126. Thus, the diameter and/or the length of the first passage may be selected such that a desired time delay is achieved. In one embodiment, the time delay is measured from the time the pin 42 is removed until medicament is dispensed from the third chamber 126.

The delivery time may be the time from when the third plunger 128 begins to move relative to the third chamber 126 until a dose of medicament is delivered to the user. The third plunger 128 may not need to travel the full distance of the third chamber 126 for a dose of medicament to be delivered. The movement of the third plunger 128 relative to the third chamber 126 may be faster than the movement of the second plunger 122 relative to the second chamber 120. In one embodiment, the time delay is longer then the delivery time. In another embodiment, the time delay is equal to the delivery time. In yet another embodiment, the time delay is less than the delivery time.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words “right”, “left”, “lower” and “upper” designate directions in the drawings to which reference is made. The words “inwardly” and “outwardly” refer to directions toward and away from, respectively, the geometric center of the drug delivery device. Unless specifically set forth herein, the terms “a”, “an” and “the” are not limited to one element but instead should be read as meaning “at least one”.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A medicament delivery device comprising:

a first chamber including a first plunger, the first plunger configured to move relative to the first chamber;

a second chamber fluidly connected to the first chamber, the second chamber including a second plunger and configured to receive fluid from the first chamber when the first plunger moves relative to the first chamber, the second plunger configured to move relative to the second chamber as the fluid is transferred from the first chamber to the second chamber;

a third chamber including a third plunger, the third chamber fluidly connected to the first chamber, wherein the third chamber is configured to contain a medicament, the third plunger configured to move relative to the third chamber after a pre-determined time delay from when the first plunger moves relative to the first chamber;

a biasing element configured to move the first plunger relative to the first chamber; and a needle coupled to the third chamber, the needle configured to provide a pathway for the medicament to flow from the third chamber to a user as the third plunger moves relative to the third chamber, wherein the first chamber includes a distal portion between a distal end of the first chamber and the first collar, wherein the first chamber includes a proximal portion between the first collar and the second collar, and wherein the first chamber includes a bypass, wherein the fluid flows from the distal portion through the bypass and into the proximal portion as the first plunger moves relative to the first chamber.

2. The medicament delivery device of claim 1, wherein the first chamber is configured to receive a fluid, wherein at least a portion of the fluid is transferred from the first chamber to the second chamber as the first plunger moves relative to the first chamber.

3. The medicament delivery device of claim 2, wherein at least a portion of the fluid is transferred from the first chamber to the third chamber as the first plunger moves relative to the first chamber.

4. The medicament delivery device of claim 3, wherein the medicament delivery device is configured to transfer the fluid from the first chamber to the second chamber before the fluid is transferred from the first chamber to the third chamber.

5. The medicament delivery device of claim 3, wherein the first plunger includes a first collar having a first collar diameter and a body having a body diameter, wherein the body diameter is less than the first collar diameter.

6. The medicament delivery device of claim 5, wherein the first plunger includes a second collar having a second collar diameter, wherein the body diameter is less than the second collar diameter.

7. The medicament delivery device of claim 2, wherein the second chamber includes a flexible membrane configured to move relative to the second chamber as the fluid is transferred from the first chamber to the second chamber.

8. The medicament delivery device of claim 2, wherein the second chamber includes a gas permeable membrane configured to allow gas to escape from the second chamber but prevent fluid from exiting the second chamber as the fluid is transferred from the first chamber to the second chamber.

9. The medicament delivery device of claim 1, wherein the transfer of the fluid into the third chamber moves the third plunger relative to the third chamber thereby expelling the medicament from the third chamber through the needle and to the user.

* * * * *